United States Patent
Safai

(10) Patent No.: US 10,830,714 B1
(45) Date of Patent: Nov. 10, 2020

(54) PORTABLE X-RAY BACKSCATTERING SYSTEM

(71) Applicant: The Boeing Company, Chicago, IL (US)

(72) Inventor: Morteza Safai, Newcastle, WA (US)

(73) Assignee: The Boeing Company, Chicago, IL (US)

( * ) Notice: Subject to any disclaimer, the term of this patent is extended or adjusted under 35 U.S.C. 154(b) by 0 days.

(21) Appl. No.: 16/522,791

(22) Filed: Jul. 26, 2019

(51) Int. Cl.
*G01T 7/00* (2006.01)
*G01N 23/203* (2006.01)
*G01V 5/00* (2006.01)

(52) U.S. Cl.
CPC ............. *G01N 23/203* (2013.01); *G01T 7/00* (2013.01); *G01V 5/0025* (2013.01)

(58) Field of Classification Search
CPC ....... G01N 23/203; G01V 5/0025; G01T 7/00
See application file for complete search history.

(56) References Cited

U.S. PATENT DOCUMENTS

| | | | |
|---|---|---|---|
| 7,535,990 B2 | 5/2009 | Safai et al. | |
| 7,567,649 B1 | 7/2009 | Safai et al. | |
| 7,623,626 B2 | 11/2009 | Safai et al. | |
| 7,649,967 B2 | 1/2010 | Jonsson | |
| 9,151,721 B2 | 10/2015 | Safai | |
| 2004/0028178 A1* | 2/2004 | Jupp | G01V 5/0025 378/64 |
| 2013/0208857 A1* | 8/2013 | Arodzero | G01T 1/2006 378/57 |
| 2015/0319832 A1* | 11/2015 | Grimshaw | H05G 1/26 378/86 |
| 2016/0341847 A1* | 11/2016 | Arroyo, Jr. | G01V 5/0025 |
| 2017/0023696 A1* | 1/2017 | Morton | G01V 5/0025 |
| 2017/0027532 A1* | 2/2017 | Joshi | A61B 6/107 |
| 2019/0293810 A1* | 9/2019 | Couture | G01T 1/2018 |
| 2020/0103547 A1* | 4/2020 | Morton | G01V 5/0016 |

\* cited by examiner

*Primary Examiner* — Mark R Gaworecki
(74) *Attorney, Agent, or Firm* — Coats & Bennett, PLLC

(57) ABSTRACT

Methods, systems, and apparatuses are disclosed for making and using a non-destructive inspection apparatus comprising a portable X-ray backscatter detection apparatus having predetermined electromagnetic radiation cancelling features in the form of deflection yokes in communication with photomultiplier tubes to improve imaging contrast in non-destructively inspecting target substrates in situ and in real time.

20 Claims, 7 Drawing Sheets

PORTABLE X-RAY BACKSCATTERING SYSTEM

TECHNOLOGICAL FIELD

The present disclosure relates generally to the field of non-destructive testing and non-destructive inspection of sub-surface regions of target structures and substrates. More specifically the present disclosure relates to the field of using small angle X-ray backscattering techniques to non-destructively inspect interlayers for characteristics that include, for example, bonding strength of composite material layers.

BACKGROUND

Presently, regulatory guidelines relating to the inspection of bonded composite materials in certain industries mandate the use of testing techniques that destroy the material being tested. This results in significant expense, as large structures that contain composite parts, such as, for example, aircraft and other vehicles, must be taken out of service, destructively inspected, and then reworked before the aircraft can be placed back into service.

Non-destructive inspection systems for evaluating substrates have found utility in industry, for example, where access to various components and substrate materials requiring routine service and inspection may be difficult to access without significant labor or without partially, or completely, destroying the component or substrate material. For a non-destructive testing method or system to supplant the mandatory destructive methods presently in use, a non-destructive testing method must insure consistently reliable and repeatable analysis of a inspected object's surface or sub-surface that at least equals or exceeds the physical determinations made during destructive testing.

X-rays are a form electromagnetic radiation, typically having a wavelength ranging from 0.01 to 10 nanometers, corresponding to frequencies ranging from 30 petahertz to 30 exahertz ($3 \times 10^{16}$ Hz to $3 \times 10^{19}$ Hz) and energies in the range of 100 eV to 100 keV. X-ray backscatter systems are a type of X-ray imaging system using the indirect detection of X-rays to inspect a target object. X-ray backscatter systems typically comprise an X-ray tube, a collimator, and a detector. The X-ray tube generates and emits X-rays. The collimator filters the X-rays to form an X-ray beam using a portion of the X-rays that travel substantially parallel to a specified direction.

When the X-ray beam encounters the target object, some, or all, of the X-rays in the X-ray beam are scattered by the target object in various directions. In particular, the X-rays may be scattered from the surface of the target object and/or from the sub-surface of the target object. The scattered X-rays are referred to as backscatter. When the backscatter impacts a detector, the detected X-ray backscatter can be used to generate image data for the target object being investigated. For example, the backscatter that is detected when the X-ray beam is directed at a particular location, on or within a particular target object, can be used to generate an intensity value for a pixel in an image that corresponds to that particular location on or within the target object. The use of X-rays for non-destructive material evaluation allows inspection without destroying parts, components, substrates, etc. being inspected.

At least due to the weight and configuration of the various components, typical X-ray backscatter systems are typically large, cumbersome and use stationary detectors having a fixed focus with typically planar shapes for collecting X-ray backscatter from an object

SUMMARY

According to a present aspect, an X-ray backscatter detection apparatus is disclosed including a housing, with the housing configured to encase components comprising at least a plurality of electronic circuits and an integrated high voltage power supply. The apparatus further includes at least one photomultiplier tube, with the photomultiplier tube configured to generate an electro-magnetic field, and said photomultiplier tube oriented externally from the housing and said at least one photomultiplier tube further oriented proximate to the housing; and at least one deflection yoke, with the deflection yoke positioned proximate to the photomultiplier tube.

According to a further aspect, the deflection yoke is configured to generate a predetermined countering electro-magnetic field, said countering-electro-magnetic field configured to at least partially counter the electro-magnetic field generated by the photomultiplier tube.

In another aspect, the photomultiplier tube integrates the deflection yoke.

In another aspect, the photomultiplier tube comprises a plurality of deflection yokes, with the plurality of deflection yokes coupled to the photomultiplier tube.

In a further aspect, the presence of the deflection yoke obviates the need for a plurality of components, said plurality of components comprising more than one of: a cooling device; a high voltage cable; a commutation cable, a control unit; a cable management device; or combinations thereof.

In another aspect, the deflection yoke is configured to generate a countering electro-magnetic field, said countering electro-magnetic field having a predetermined intensity and value.

In another aspect, the X-ray backscatter detection apparatus has a footprint sufficient to achieve a portable X-ray backscatter detection apparatus footprint for the presently disclosed X-ray backscatter detection apparatus.

In another aspect, a method of making an X-ray backscatter detection apparatus is disclosed, with the method including integrating a plurality of X-ray backscatter detection components into a housing that can be a unitary housing, with the housing including a housing exterior, and with the plurality of X-ray backscatter detection components including: a high voltage power supply, a plurality of electronic circuits, and an X-ray generating source. The method further includes orienting at least one scintillator detector proximate to the housing exterior, orienting at least one photomultiplier tube proximate to the scintillator detector, and orienting at least one deflector yoke proximate to the photomultiplier tube. The terms "scintillator" and "scintillator detector" are used equivalently and interchangeably herein generally and when referring specifically to enumerated part 26.

In another aspect, a method of making an X-ray backscatter detection apparatus is disclosed, with the method including integrating a plurality of X-ray backscatter detection components into a housing, with the housing including a housing exterior, and with the plurality of X-ray backscatter detection components including: a high voltage power supply; a plurality of electronic circuits; and an X-ray generating source. The method further includes orienting at least one scintillator detector proximate to the housing exterior, orienting at least one photomultiplier tube (18)

proximate to the scintillator detector; and orienting at least one deflector yoke (20) proximate to the photomultiplier tube.

In another aspect, a method further includes coupling at least one deflection yoke to a photomultiplier tube, and wherein the deflection yoke is configured to generate a predetermined countering electro-magnetic field, with the countering-electro-magnetic field configured to at least partially counter the electro-magnetic field generated by the photomultiplier tube, and generating a predetermined countering electro-magnetic field, said predetermined countering-electro-magnetic field configured to at least partially counter an electro-magnetic field generated by the photomultiplier tube.

In another aspect, a method further includes coupling a plurality of deflection yokes to the photomultiplier tube.

In another aspect, a method further includes coupling a plurality of deflection yokes to a plurality of photomultiplier tubes.

In another aspect, a method of non-destructively inspecting a substrate is disclosed, with the method including orienting an X-ray backscatter detection apparatus proximate to a substrate, with the integrated X-ray backscatter detection apparatus including: an integrated X-ray source, an integrated collimator, an integrated high voltage power supply, at least one scintillator detector, at least one photomultiplier tube, with the photomultiplier tube configured to generate an electro-magnetic field; and at least one deflection yoke oriented proximate to the photomultiplier tube, with the deflection yoke configured to generate a predetermined countering electro-magnetic field, and delivering an X-ray beam to the substrate. The method further includes collecting an amount of X-ray backscatter at the scintillator detector, generating an image signal, and sending the image signal to a readout.

The features, functions and advantages that have been discussed can be achieved independently in various aspects or may be combined in yet other aspects, further details of which can be seen with reference to the following description and the drawings.

BRIEF DESCRIPTION OF THE DRAWINGS

Figure 1:
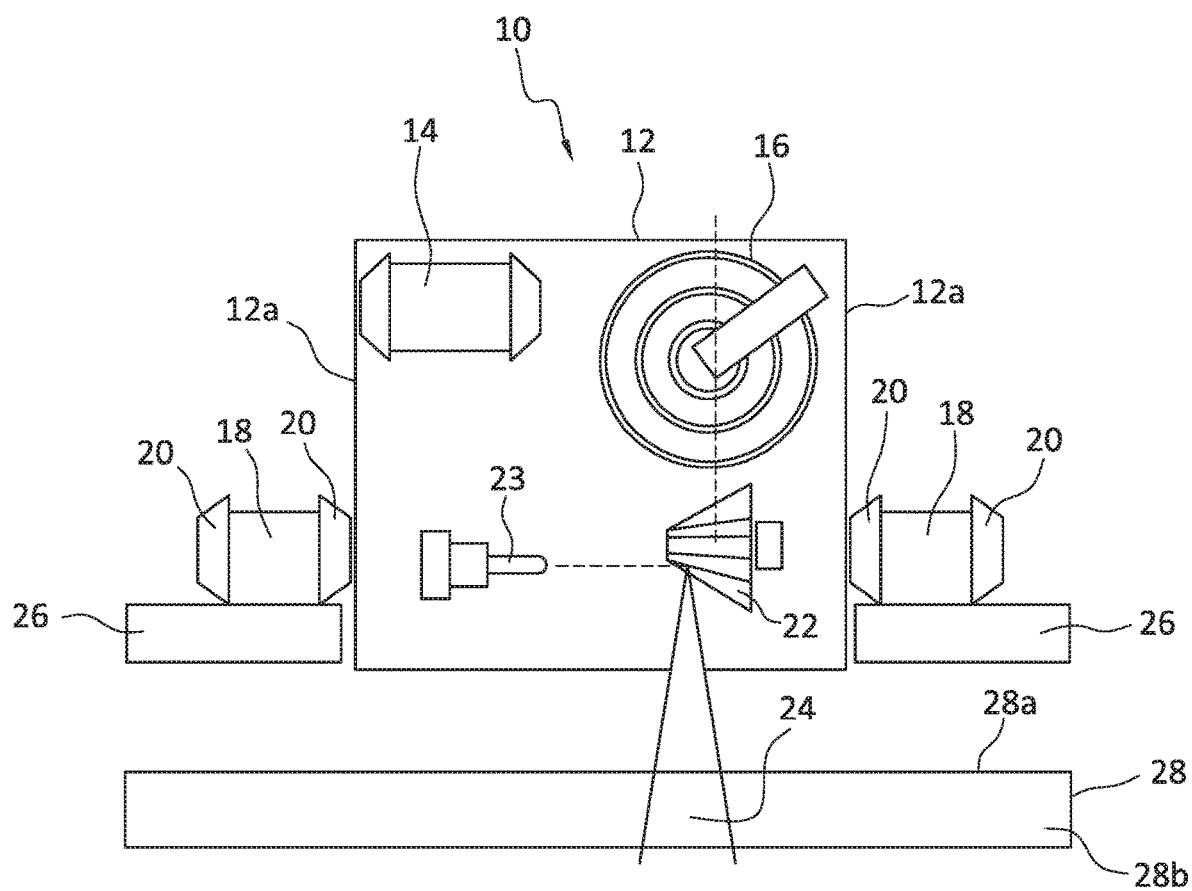
Figure 2:
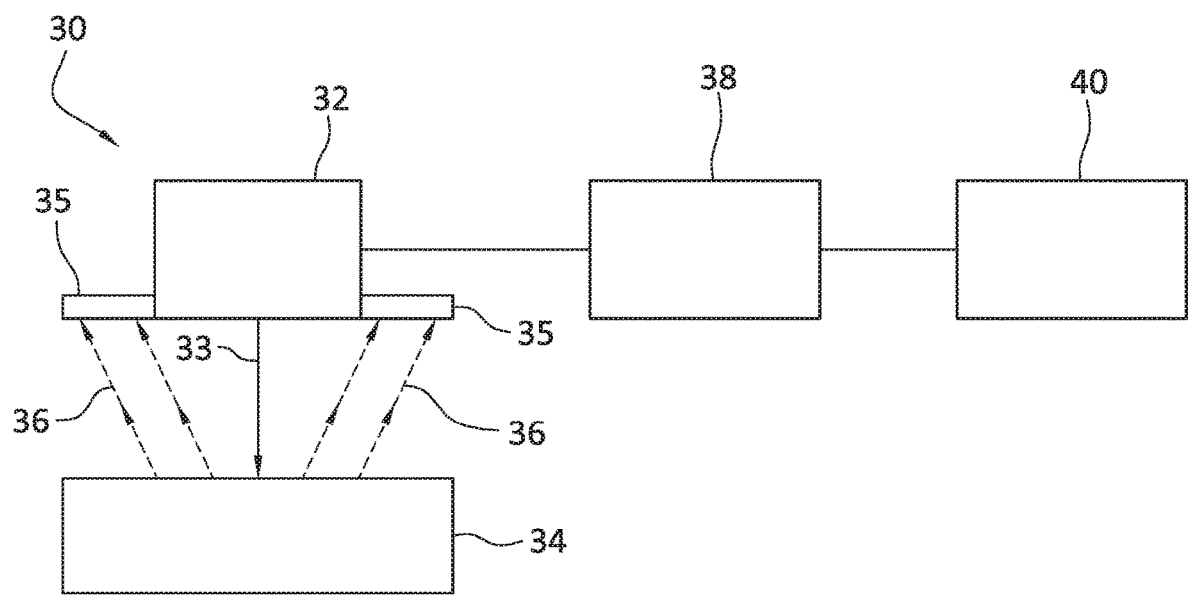
Figure 3:
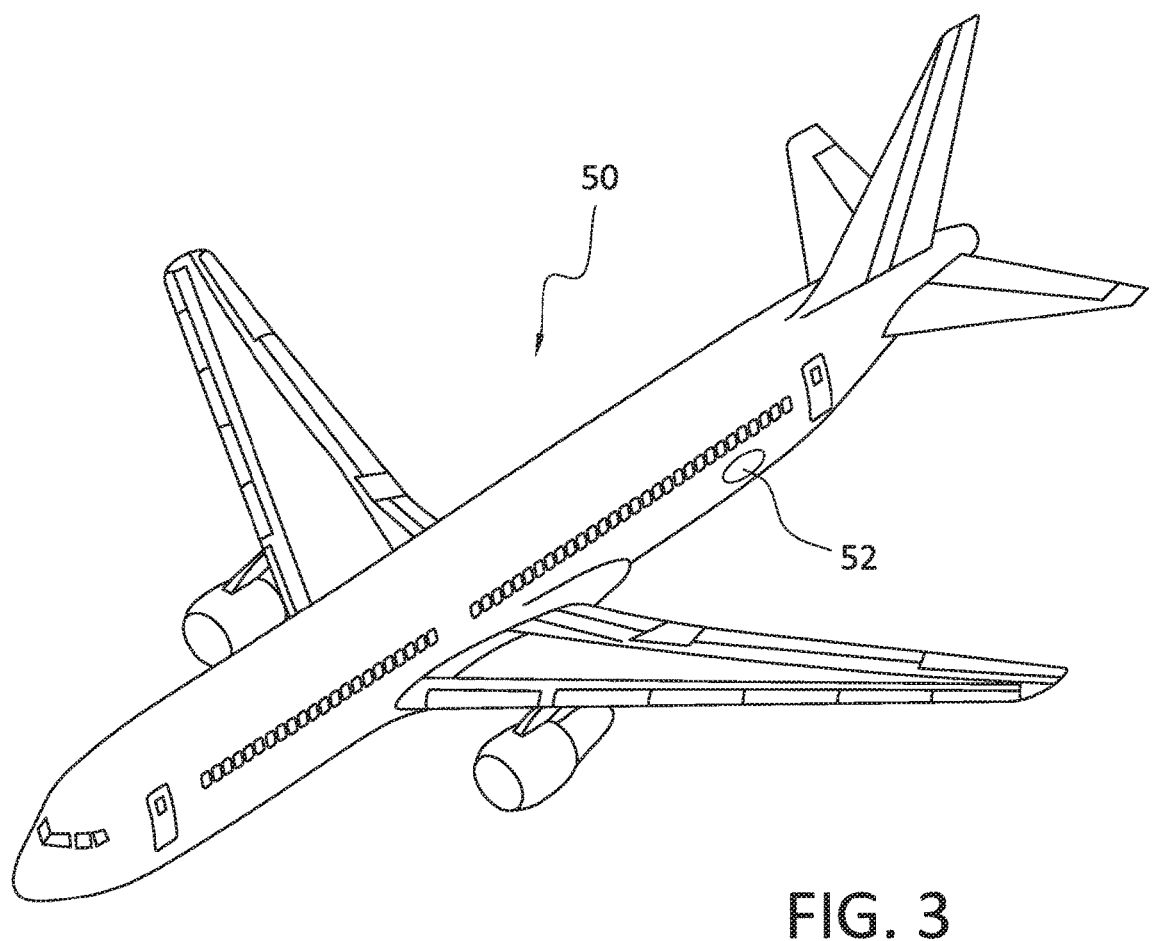
Figure 4:
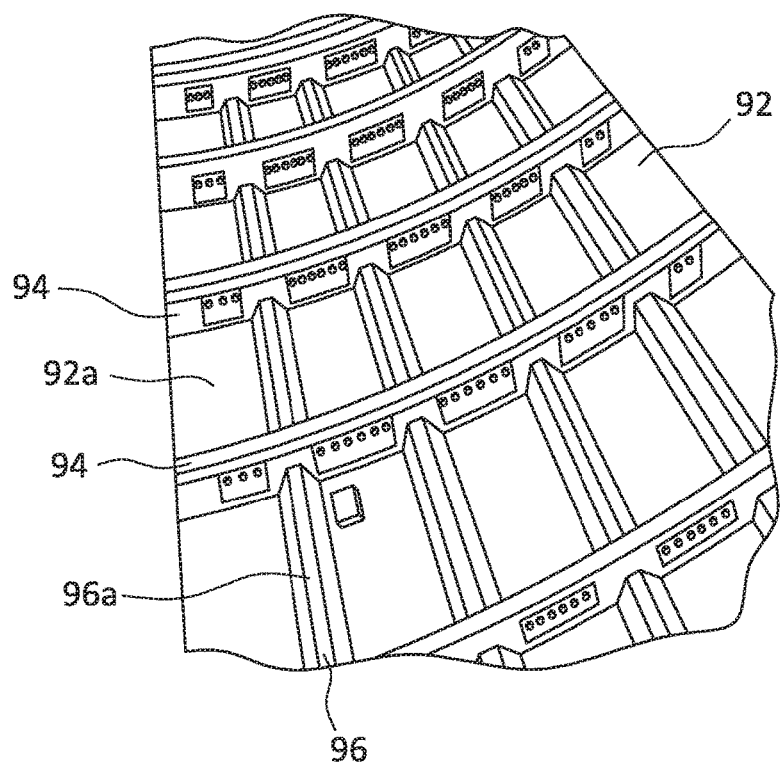
Figure 5:
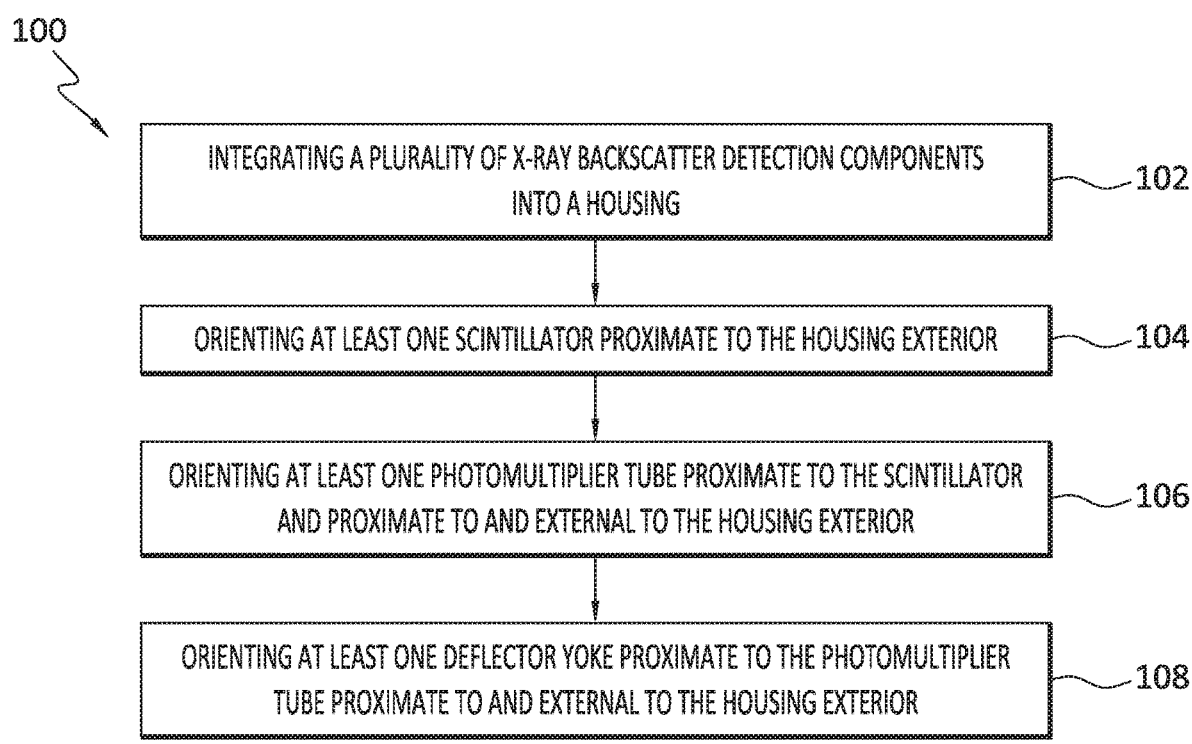
Figure 6:
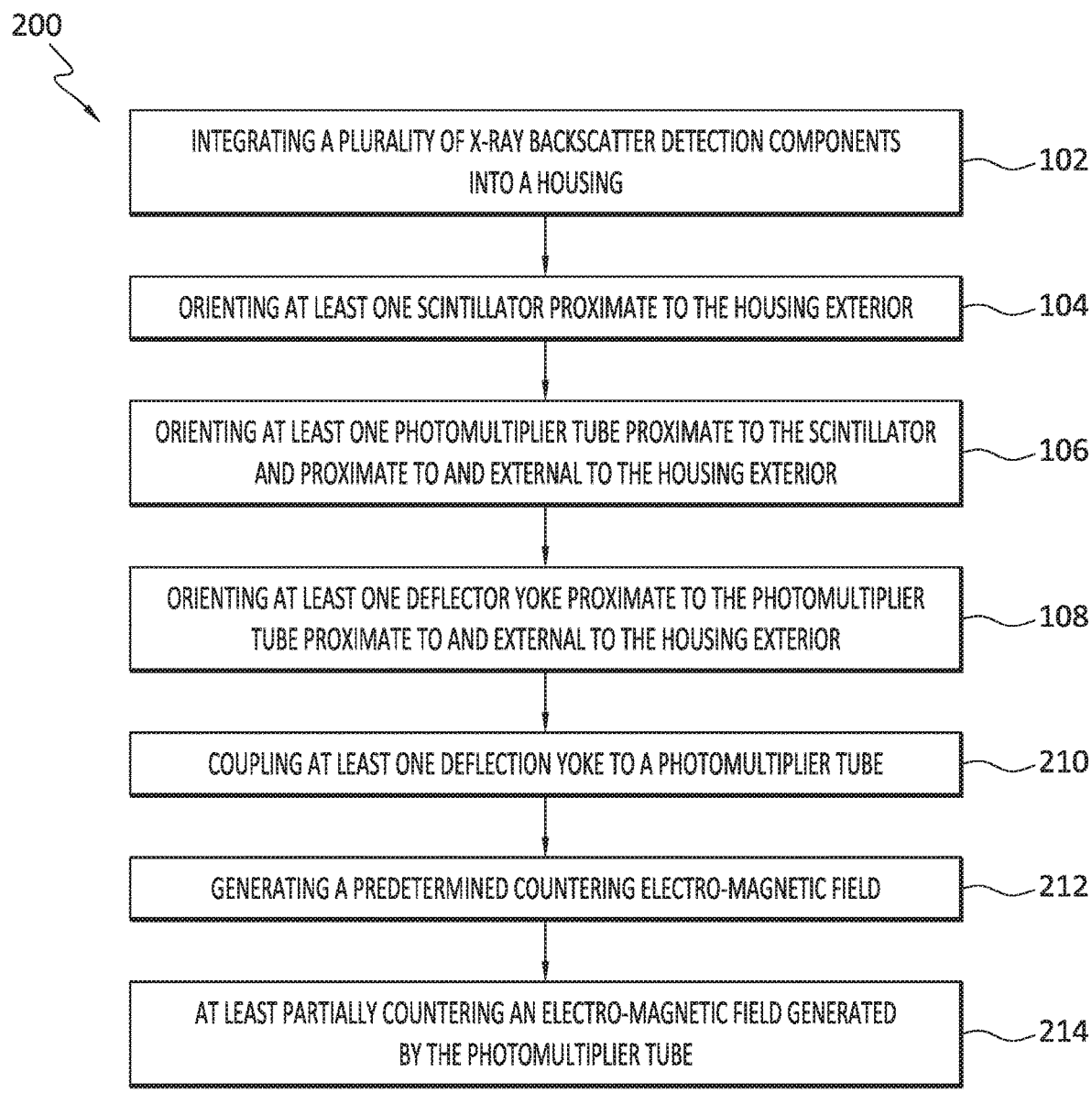
Figure 7:
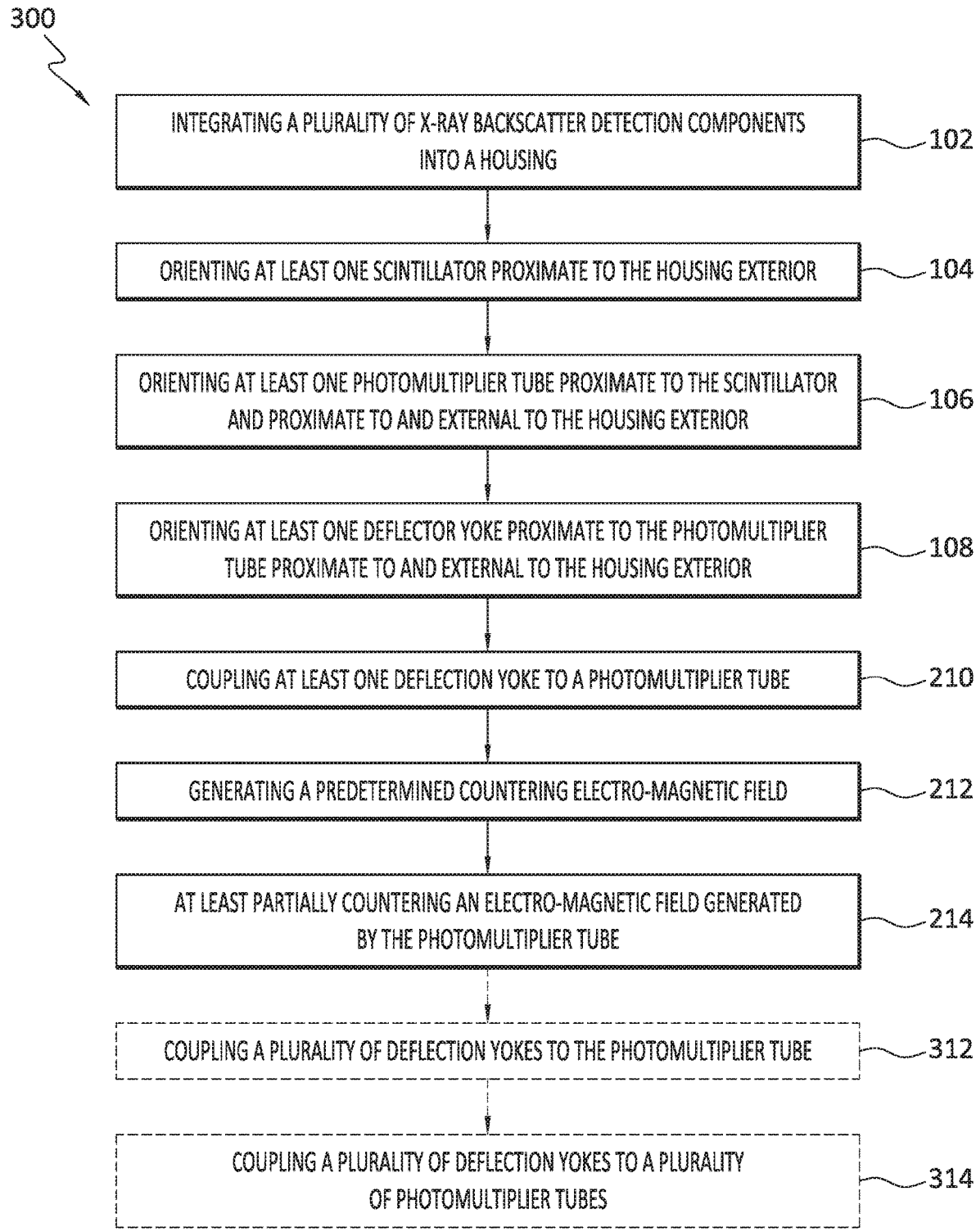
Figure 8:
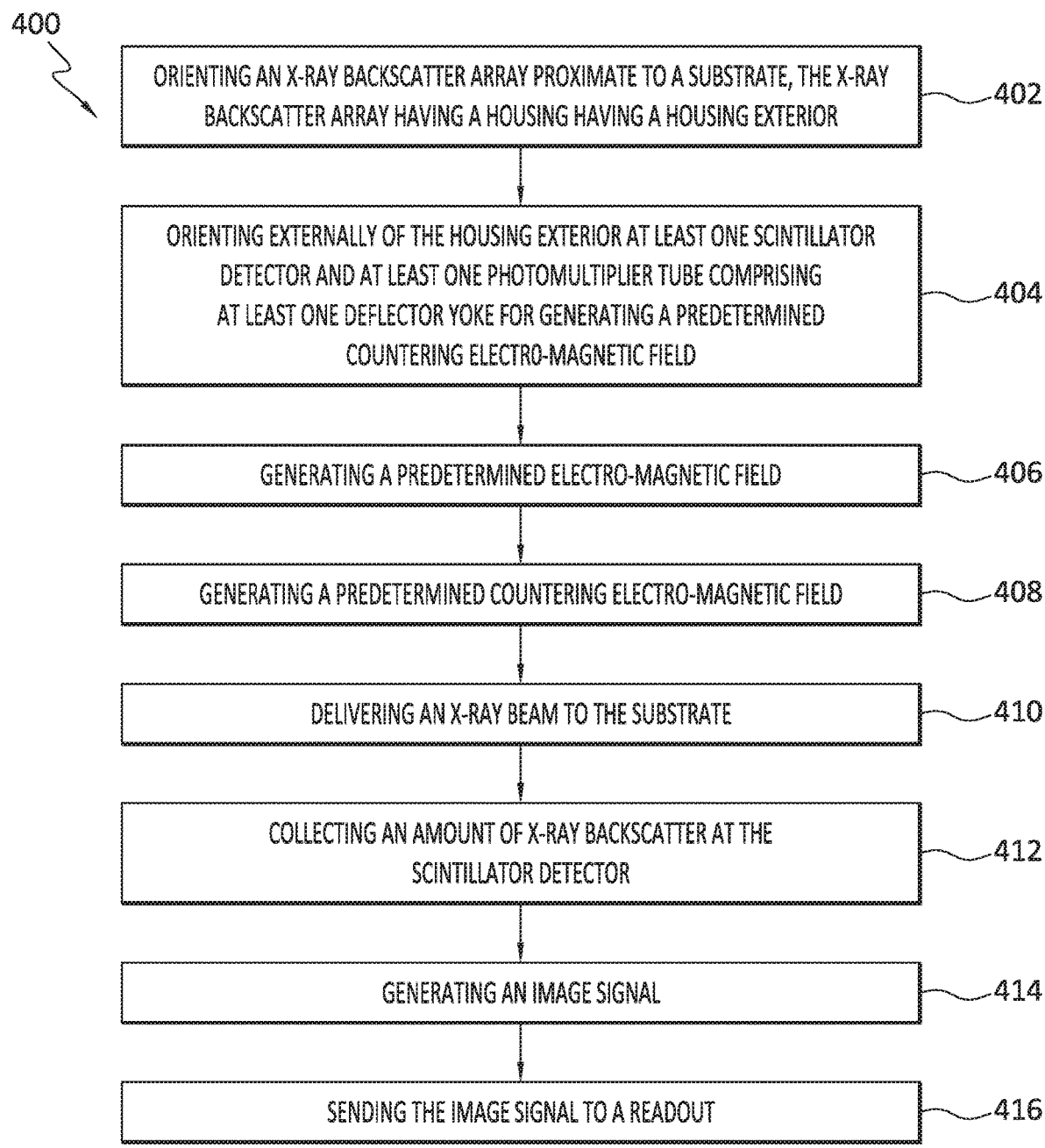

Having thus described variations of the disclosure in general terms, reference will now be made to the accompanying drawings, which are not necessarily drawn to scale, and wherein:

FIG. 1 is non-limiting diagram of a portable X-ray backscatter detection apparatus according to a present aspect;

FIG. 2 is non-limiting diagram of a is a portable X-ray backscatter detection apparatus according to a present aspect;

FIG. 3 is a non-limiting illustration of a vehicle in the form of an aircraft according to a present aspect;

FIG. 4 is a non-limiting illustration of an interior portion of a vehicle in the form of a fuselage interior according to a present aspect;

FIG. 5 is a non-limiting flowchart outlining a method according to a present aspect;

FIG. 6 is a non-limiting flowchart outlining a method according to a present aspect;

FIG. 7 is a non-limiting flowchart outlining a method according to a present aspect; and FIG. 8 is a non-limiting flowchart outlining a method according to a present aspect.

DETAILED DESCRIPTION

X-ray backscatter analysis is a type of X-ray imaging that allows an evaluator to use X-rays to indirectly inspect an object by directing an X-ray beam at an object, and indirectly collecting X-ray backscatter as readings on a detection device, as the X-rays are scattered as "backscatter" from the target object. When signals generated from collected X-ray backscatter are interpreted via appropriate software, X-ray backscatter techniques can yield a viewable image of a region of target-object, for example, for the purpose of detecting flaws or otherwise characterizing a target object region such as, for example, a target object surface and/or a target object sub-surface.

Depending on the shape of the target object, X-ray backscatter systems may not comprise adequate resolution for determining features of a target object. For example, images generated from signals generated by an X-ray detector and sent to an X-ray imaging system may not provide a desired contrast (e.g., images may not be sharp enough or clear enough) to enable one to reliably detect anomalies of a certain size that could cause a target object to fail inspection. Further, typical X-ray backscatter systems are typically large, cumbersome and use stationary detectors having a fixed focus with typically planar shapes for collecting X-ray backscatter from an object.

In a typical X-ray backscatter protocol and system, the X-ray beam can be moved relative to the target object in a selected pattern such as, for example, a raster patter, such that image data can be generated for different locations on or within the target object. The image data can then form one or more images that can be interpreted using computing software and hardware for determining whether inconsistencies, anomalies, defects, etc. reside in the locale of the target object inspected by the X-ray backscatter system.

The typical size, or "footprint" of X-ray backscatter detectors can limit the practical usefulness of X-ray backscatter inspection regimes. In some cases, typical X-ray backscatter detection systems can weigh 1000 lbs or more, and typically require stationary testing at the site of the instrument. That is, in situ non-destructive inspection for large structures is typically complicated by the footprint (referred to equivalently herein as a "physical footprint") and size of the inspection instruments (e.g., apparatuses), methods, and systems. In addition, if the target object surface has a complex geometry, or the target surface resides in a location that is difficult to access, X-ray backscatter detectors may be difficult to employ.

Further, typical designs for X-ray backscatter systems require a multitude of components that used in generating the required amount and intensity of emitted electromagnetic radiation (EMR) in the form of X-rays. For example, the large power supply required to operate a 160,000 Volt X-ray tube typically required for X-ray backscatter detectors is typically integrated into the instrument. In addition, components such as cooling devices, high voltage cables, communication cables, control units, cable management devices, etc., are typically further integrated into X-ray backscatter detectors, further adding to the complexity, weight and overall size or "footprint" of the system. In addition, when such components are powered to operate, such components generate electronic signatures that can contribute to system "noise" that can interfere with the recordings and readings of the scintillator detector(s) that detect backscatter.

According to present aspects, improved X-ray backscatter detection apparatuses are disclosed that house certain components within a housing and relegate further components to a location outside of the housing. In addition, present aspects provide noise cancellation of certain integrated components by providing and orienting deflector yokes proximate to the photomultiplier tubes associated with the scintillator detectors(s). The deflector yokes are fashioned to provide a desired and predetermined cancellation effect to EMR signals, and provide noise cancellation that results in improved scintillator readings that leads to improved resolution of readout images by improving, for example, image contrast, etc. The predetermined electro-magnetic field cancellation effect, that can be at least a predetermined partial electro-magnetic cancellation effect can be accomplished by manufacturing, adapting, modifying, etc., the deflector yokes by, for example, providing a predetermined amount of wire wound around the deflector yoke (or providing a predetermined amount of other material to the deflector yoke, with the material provided to the yoke configured to generate a predetermined electro-magnetic field that can be a tailorable electro-magnetic field) or other material for the purpose of creating the desired and predetermined electro-magnetic cancellation or countering effect(s) with respect to the electro-magnetic field or fields created by powered components of the X-ray backscatter detection apparatus during operation of the X-ray backscatter detection apparatus. For present purposes, the terms "predetermined electro-magnetic cancellation effect", "electro-magnetic cancelling effect" and "electromagnetic countering effect" are equivalent terms that are intended to be used interchangeably when describing predetermined electro-magnetic fields and predetermined countering electro-magnetic fields. As presently contemplated herein, the electro-magnetic fields and countering electro-magnetic fields have electromagnetic field values and countering electro-magnetic field values, that can both be predetermined values.

In addition, the orientation of components within and outside of a housing eliminates the need for multiple components, including, at least the elimination of formerly required cooling devices, high voltage cables, communication cables, control units, cable management devices, etc. By eliminating such components from an X-ray backscatter detector system, the overall complexity of the system is reduced, the system is significantly simplified, and the overall weight and "footprint" of the system is significantly reduced to an overall weight ranging from about 200 to about 300 lbs. This weight reduction allows the presently disclosed X-ray backscatter systems to be operated, for example, by weight bearing robots or other operated mechanical positioning devices, such that the presently disclosed X-ray backscatter detectors are classified as "portable" systems. That is, according to present aspects, the term "portable" as used in the present application refers to a weight of the non-destructive X-ray backscattering system and/or apparatus (e.g., including the system and/or apparatus used in the presently disclosed methods) ranging from about 200 lbs. to about 300 lbs.

In addition, by eliminating a number of electronic and other electrically powered components from the X-ray backscatter system, significantly improved X-ray backscatter imaging is achieved. Further, with a reduced number of electrically powered components, the EMRs that can interfere with the scintillation detectors can be determined, accounted for and cancelled through the positioning of deflector yokes positioned proximate to or incorporated with the photomultiplier tubes.

The scintillator detectors disclosed herein can be those used in conjunction with the presently disclosed X-ray backscattering methods, systems, and apparatuses, and comprise scintillating layers comprising scintillating materials that are deposited onto or otherwise incorporated into the X-ray backscattering detectors. The scintillating materials absorb the backscattered X-rays and convert the X-ray radiation into visible light. Photodetectors present in the detectors that are sensitive to visible light convert the light from the scintillator into electric signals that are interpreted into visual images. The scintillating coatings can be, for example, at least one thin continuous layer or layer of scintillating material.

The present X-ray backscattering detector substrate is made from materials, and can be dimensioned, such that the X-ray backscattering detector can be highly flexible, to the extent that the X-ray backscattering detector substrate comprising a scintillating material layer that can be oriented and otherwise shaped into a desired non-planar geometry that, for example, complements, closely approximates, and/or substantially matches the geometry of the target substrate (referred to equivalently here as the "target object"), including but not limited to the geometry of the target substrate surface. The target substrate geometry can include a planar geometry, or the target substrate geometry can include a non-planar geometry including, for example, one or more of a concave geometry, a convex geometry, an irregular geometry or geometries, a complex non-planar geometry, and combinations thereof, etc.

In accordance with a present aspects, where reduced weight of the overall X-ray backscattering system is desired, presently disclosed X-ray backscatter detection apparatuses, systems, and methods can further benefit from the use of very thin detector substrates that comprise a continuous thin layer of scintillating material, with the scintillating material substantially covering at least one surface of the flexible detector substrate. The presently disclosed X-ray backscattering detectors that include the detector substrate and the scintillating material layer can be selected and fabricated to a total flexible detector thickness preferably ranging from about 50 μm to about 100 μm, although thicker scintillating material layers can be used, if desired.

According to present aspects, X-ray backscatter techniques, and the resolution and contrast of the X-ray backscatter imaging made possible through the use of the presently disclosed X-ray backscattering methods, apparatuses, and systems, are significantly improved through the use of the deflector yokes configured to effectively counter or "cancel" a predetermined amount of EMR emitted from various sources in the system.

Accordingly, presently disclosed non-destructive X-ray backscatter detection apparatuses, systems, and methods, provide improved inspection imaging signaling and resulting image by measuring or otherwise determining and taking into account, the existing electromagnetic radiation introduced into the apparatus and system by the various components of the apparatus. Once the level of or amount of potentially interfering electromagnetic radiation is determined, deflector yoke are tailored to produce a countering level of electromagnetic radiation for the purpose of "cancelling out" or otherwise neutralizing the extraneous system "noise" caused by the presence of interfering electromagnetic radiation introduced into such systems and apparatuses.

According to further present aspects, the tailored deflector yokes are constructed with materials and into orientations that provide a requisite countering electromagnetic radiation force, such as, for example, by providing an amount or degree of metallic or other material "windings". Additional present aspects further work to ameliorate the presence of interfering electromagnetic radiation by orienting various system components (capable of emitting a particular level of electromagnetic radiation) inside of a housing. The apparatus housing can comprise a shielding or other material layer or layers for the purpose of reducing extraneous electromagnetic radiation that could otherwise interfere with the scintillators or otherwise interfere with the signals sent by the scintillators that are to be interpreted by the computing function of the apparatus, and that otherwise contribute to "noise" that reduces contrast or otherwise adversely impacts the resolution of the imaging signals that can be viewed at the system or apparatus viewing output.

Further, the orientation of certain system and apparatus components within or outside of the housing, coupled with the countering influence of deflector yoke that is oriented proximate to the photomultiplier tubes outside of the housing, obviates the need for various system and apparatus components including, for example, a cooling device; a high voltage cable; a commutation cable, a control unit; a cable management device; etc. or combinations thereof. By eliminating the presence of at least the aforementioned components, the generation of interfering electromagnetic radiation that would otherwise be present if such components reduces the amount of countering EMR that must be produced, and further improves the resolution and contrast of imaging signals and the viewable images that are produced the present systems.

The methods, systems, and apparatuses disclosed herein greatly improve non-destructive X-ray inspection techniques, including indirect non-destructive X-ray backscattering techniques for evaluating and inspecting target surfaces, including target surfaces that are non-planar or that include non-planar target geometries. As used herein, the term "non-planar" in the context of "non-planar" surfaces, are defined as surfaces that have at least an area that is not entirely lying or able to be confined within a single plane. According to present aspects, such non-planar targets and target surfaces further include, in non-limiting fashion, geometries including: a concave geometry, a convex geometry, an irregular geometry, geometries comprising contour including complex contours, other complex geometries, and combinations thereof.

According to present aspects, the X-ray backscatter detector substrate can be made from a material such as, for example, an organic carbon-containing material, including, for example, polyethylene naphthalate, poly-4-vinylphenol, and combinations thereof.

According to present aspects, the scintillating material can be deposited onto the X-ray backscatter detector substrate (that can be a flexible substrate) to achieve a scintillating material layer on the scintillator having an average thickness ranging from about 200 nm to about 50 µm. Still further, the scintillating material layer can be deposited onto a thin, flexible X-ray backscatter detector substrate, for example, via an additive manufacturing method for depositing thin films, including, for example, inkjet printing methods. When inkjet printing techniques are used to deposit the scintillating material onto the flexible substrates, the scintillating material is provided to an inkjet printer in the form of a scintillating inkjet printing ink. Any scintillating material that can be formulated into an inkjet print ink can be used to make the scintillating layer. Particularly preferred scintillating material layers can include, for example, inkjet printer deposited or "printed" formulations based on gadolinium oxide doped with europium ($Gd_2O_3$: $Eu^{3+}$); gadolinium oxysulfate (GdOS); cesium iodide (CsI), and calcium tungstate ($CaWO_4$).

Present non-limiting aspects are illustrated in FIG. 1. As shown in FIG. 1, a portable non-destructive X-ray backscatter inspection system 10 comprises a housing 12 with a housing exterior 12a, with the housing 12 configured to enclose system components that include: electronic circuits 14, a high voltage power supply 16 an x-ray radiation source 22 and a filament 23 (with the filament 23 and the X-ray radiation source 22 together comprising the X-ray radiation source). Though not shown, the X-ray radiation source is further understood to include an X-ray radiation tube positioned within a collimator, with the collimator having an aperture. In operation, as X-rays 24 are emitted from the X-ray radiation source 22 (that can be, for example, an X-ray tube or part of an X-ray tube), a collimator can rotate such that an aperture changes position and directs emitted X-rays 24 to different positions on a target substrate 28. A target substrate, as shown in FIG. 1, comprises a target substrate surface 28a and a target substrate sub-surface 28b. The terms "X-ray source" and "X-ray radiation source" and "X-ray generating source" are used equivalently herein generally, and when referring to "part" enumerated as 22".

According to present aspects, FIG. 1 further shows a number of system components oriented externally from the housing 12 and oriented proximate to the housing exterior 12a, with such components oriented externally from the housing 12 and oriented proximate to the housing exterior 12a including a plurality of photomultiplier tubes 18 with a plurality of deflector yokes 20 shown oriented proximate to the photomultiplier tubes 18, and with the photomultiplier tubes oriented proximate to a scintillator 26.

FIG. 2 is a diagram further illustrating, in non-limiting fashion, an X-ray backscattering system 30 according to further present aspects. As shown in FIG. 2, an X-ray backscattering system 30 that can be a portable X-ray backscattering system 30, includes a portable X-ray backscatter detector 32 that can be configured to direct X-ray radiation in the form of X-ray beams 33 from an X-ray source 22 (such as that shown in FIG. 1, etc., though not explicitly shown in FIG. 2) toward a target substrate 34. As further shown in FIG. 2, reflected X-ray beams 36 are directed as backscatter from the target substrate 34 to the scintillators 35. Signals are generated at and/or by the scintillator and then sent from the portable X-ray backscatter detector 32 to a computer 38 comprising interpreting software/hardware that can be configured to interpret the signals so received, and convert the signals received from the scintillator to imaging signals 39. Imaging signals 39 are then directed to a visual readout 40, that can be in the form of, for example, a computer monitor, a handheld device, etc. from which visual images can be viewed, recorded, etc. Visual readout can be located proximate to the system 30, or can be located at a distance remotely from the system and in communication with the system via a wireless technology such as, for example, Wi-Fi, Bluetooth, etc.

The target substrate to be non-destructively inspected according to presently disclosed methods, using presently disclosed systems, and apparatuses can be made from any material. For example, the portable X-ray backscattering systems can non-destructively inspect metallic materials, non-metallic materials and combinations thereof. Non-limiting examples of non-metallic materials include, for example, composite materials and materials and material layers that exist between metallic and/or non-metallic materials, including, for example, adhesive layers (e.g., adhesive materials that may be cured, and that may be in the form of, for example, material bond lines, etc.) existing within or adjacent to composite material, including composite laminate materials. That is, according to present aspects, the portable X-ray backscattering methods, systems, and apparatuses can be configured to non-destructively inspect bond lines in target substrate materials in situ, and in real time, including bond lines in composite materials, or bond lines between a composite material (or other non-metallic material) and a metallic material.

The target substrates can include discrete components (equivalently referred to herein as "parts"), as well as components incorporated into larger assemblies, sub-assemblies, etc., that can be non-destructively inspected in situ and in real time, according to present aspects. A non-exhaustive list of objects benefiting from the presently disclosed non-destructive inspection methods, systems, and apparatuses include, for example, metallic and non-metallic parts, used in the manufacture of stationary structures including buildings, bridges, trusses, piping, pipes, and pipelines, ducts, etc., including pipes, piping, and pipelines used in connection with petroleum product or other chemical product (including, for example, water) pipelines, as well as vehicles including, for example, manned and unmanned aircraft, manned and unmanned spacecraft, manned and unmanned rotorcraft, manned and unmanned terrestrial vehicles, manned and unmanned surface water borne vehicles, manned and unmanned sub-surface water borne vehicles, satellites, etc.

FIG. 3 is a non-limiting illustration of a vehicle 50 in the form of an aircraft, with the vehicle/aircraft comprising a fuselage 52. FIG. 4, according to a present aspect, shows a non-limiting illustration of a fuselage interior 92a of fuselage 52 showing frames 94 and stringers 96. According to present aspects, surface and sub-surface regions of the frames and stringers, as well as the fuselage itself can be non-destructively inspected as target surfaces. The target surfaces exemplified in FIGS. 3 and/or 4 can be non-destructively inspected using the portable X-ray backscattering systems illustrated in any of FIGS. 1 and 2.

FIG. 5 is a flowchart outlining a non-limiting method, according to present aspects, for non-destructively inspecting a target surface is shown using the portable X-ray backscattering systems illustrated in any of FIGS. 1, 2, 3, and 4. As shown in FIG. 5, a method 100 is outlined according to present aspects, including integrating 102 a plurality of X-ray backscatter detection components into a housing 12, said housing comprising a housing exterior 12a, said plurality of X-ray backscatter detection components comprising: a high voltage power supply 16; a plurality of electronic circuits 14; and an X-ray generating source 22. The method further includes orienting 104 at least one scintillator 26 proximate to the housing exterior 12a, orienting 106 at least one photomultiplier tube 18 proximate to the scintillator 26, and orienting 108 at least one deflector yoke 20 proximate to the photomultiplier tube 18.

FIG. 6 is a flowchart outlining a non-limiting method, according to present aspects, for non-destructively inspecting a target surface, with the method showing using the portable X-ray backscattering systems illustrated in any of FIGS. 1, 2, 3, and 4, as well as incorporating the method outlined in FIG. 5. As shown in FIG. 6, a method 200 is outlined according to present aspects, including integrating 102 a plurality of X-ray backscatter detection components into a housing 12, said housing comprising a housing exterior 12a, said plurality of X-ray backscatter detection components including: a high voltage power supply 16; a plurality of electronic circuits 14; and an X-ray generating source 22. The method further includes orienting 104 at least one scintillator 26 proximate to the housing exterior, orienting 106 at least one photomultiplier tube 18 proximate to the scintillator 26, and orienting 108 at least one deflector yoke 20 proximate to the photomultiplier tube 18. The method 200 as shown in FIG. 6 further includes coupling 210 at least one deflection yoke to a photomultiplier tube, wherein said deflection yoke is configured to generate a predetermined countering electro-magnetic field, said countering-electromagnetic field configured to at least partially counter the electro-magnetic field generated by the photomultiplier tube. The method further includes generating 212 a predetermined countering electro-magnetic field, with the predetermined countering-electro-magnetic field configured to at least partially counter an electro-magnetic field generated by the photomultiplier tube, and at least partially countering 214 an electro-magnetic field generated by the photomultiplier tube.

FIG. 7 is a flowchart outlining a non-limiting method, according to present aspects, for non-destructively inspecting a target surface with a method using the portable X-ray backscattering systems illustrated in any of FIGS. 1, 2, 3, 4, as well as incorporating the methods outlined in any of FIGS. 5 and 6. As shown in FIG. 7, a method 300 is outlined according to present aspects, including integrating 102 a plurality of X-ray backscatter detection components into a housing 12, with the housing comprising a housing exterior 12a, and with the plurality of X-ray backscatter detection components comprising: a high voltage power supply 16; a plurality of electronic circuits 14; and an X-ray generating source 22. The method further includes orienting 104 at least one scintillator 26 proximate to the housing exterior, orienting 106 at least one photomultiplier tube 18 proximate to the scintillator, and orienting 108 at least one deflector yoke 20 proximate to the photomultiplier tube. The method 200 as shown in FIG. 7 further includes coupling 210 at least one deflection yoke to a photomultiplier tube, wherein said deflection yoke is configured to generate a predetermined countering electro-magnetic field, said countering-electromagnetic field configured to at least partially counter the electro-magnetic field generated by the photomultiplier tube, generating 212 a predetermined countering electro-magnetic field, said predetermined countering-electro-magnetic field configured to at least partially counter an electro-magnetic field generated by the photomultiplier tube, and at least partially countering 214 an electro-magnetic field generated by the photomultiplier tube. As shown in FIG. 7, the outlined method further includes optionally coupling 312 a plurality of deflection yokes to the photomultiplier tube. When the present methods, systems, and apparatuses employ a plurality of photomultiplier tubes, the method outlined in FIG. 7 can further optionally include coupling 314 a plurality of deflection yokes to a plurality of photomultiplier tubes.

FIG. 8 is a flowchart outlining a non-limiting method, according to present aspects, for non-destructively inspecting a target surface, with the method showing using the portable X-ray backscattering detection systems illustrated in any of FIGS. 1, 2, 3, and 4, as well as incorporating the methods outlined in any of FIGS. 5, 6, and 7. As shown in FIG. 8, a method 400 is outlined according to present aspects, including orienting 402 an X-ray backscatter detection apparatus proximate to a substrate, with the X-ray backscatter detection apparatus comprising a housing, with the housing comprising a housing exterior, and with the X-ray backscatter detection apparatus including, within the housing, various components including: an integrated X-ray source; an integrated collimator; and an integrated high voltage power supply. Method 400 further includes orienting 404 externally of the housing exterior at least one photomultiplier tube, with the photomultiplier tube configured to generate an electro-magnetic field; at least one deflection yoke oriented proximate to the photomultiplier tube, and with the deflection yoke configured to generate a predetermined countering electro-magnetic field having a predetermined value; and at least one scintillator detector. According to present aspects, as shown in FIG. 8 method 400 further includes generating 406 a predetermined electro-magnetic field, generating 408 a predetermined countering electro-magnetic field, that can be an at least partially countering electro-magnetic field, and delivering 410 an X-ray beam to the substrate, collecting 412 an amount of X-ray backscatter at the scintillator detector, generating 414 an image signal, and sending 416 the image signal to a readout.

According to further present aspects, as the detector collects and records the photon energy and generates image data in the form of image data signals, the presently disclosed portable X-ray backscattering detection systems and the presently disclosed portable X-ray backscattering detection apparatuses generate and send image data signals to computer imaging systems, such as those that are commercially available, or computer imaging systems that can be further modified.

According to a further non-limiting aspect, deposition of scintillating material layers onto the scintillator(s) can be accomplished by any method that is able to deposit a substantially uniform scintillating material layer having an average thickness ranging from about 200 nm to about 50 µm. According to one present aspect, inkjet printing of the scintillating material can be accomplished by using, for example, a Dimitrix Materials Printer (DMP 2831 (Fujifilm Dimatrix, Inc.). In a preferred aspect, the inkjet printer can have a 16-nozzle piezoelectric printhead having a drop volume of about 10 pL and a spacing between nozzles of about 250 µm. Printing can be conducted with a maximum jetting frequency of about 5 kH.

According to further present non-limiting aspects, a useful polymer-based scintillating ink can be gadolinium oxide doped with europium ($Gd_2O_2$:$Eu^{3+}$) as a scintillating material. The scintillating material can be combined with a thermoplastic elastomer copolymer as a polymer matrix to produce a flexible scintillating ink with adhesive properties necessary to adhere to the flexible detector substrate. One useful thermoplastic elastomer copolymer includes, for example, styrene-ethylene/butylene-styrene (SEBS) Calprene CH-6120 (Dynasol, Houston, Tex.) having an average molecular weight of 245.33 g/mol and present in a ratio of ethylene-butylene:styrene of 68:32.

According to present aspects, when the disclosed methods and systems orient the presently disclosed portable X-ray backscattering detector proximate to a target. The target can have a target surface geometry and the portable X-ray backscattering detector can include an X-ray radiation source configured to emit X-rays, a collimator in communication with the X-ray radiation source, and with the collimator configured to form a X-ray beam using at least a portion of the X-ray radiation emitted from the X-ray radiation source. The portable X-ray backscatter detector is configured to detect X-ray backscatter formed in response to the X-ray beam encountering a target substrate. The portable X-ray backscatter detector includes an X-ray scintillator substrate that is preferably a continuous X-ray scintillator substrate and at least one layer of X-ray scintillating material configured to substantially cover the X-ray scintillator substrate (that, for example, can be a flexible X-ray scintillator substrate).

The presently disclosed methods, systems, and apparatuses provide enhanced non-destructive inspection techniques on targets such as components and parts that are difficult to inspect and can be otherwise difficult to access. Such objects can include components and parts in vehicles as well as components and parts in stationary objects and systems including, for example, and without limitation, pipes used in pipelines, storage tanks, structural supports in buildings, bridges, railways, trusses, etc. Non-destructive inspection of vehicles and components in vehicles can include, for example, and without limitation, components and assemblies incorporated into manned and unmanned aircraft, manned and unmanned spacecraft, manned and unmanned rotorcraft, manned and unmanned terrestrial vehicles, manned and unmanned non-terrestrial vehicles, manned and unmanned surface water-borne vehicles and manned and unmanned sub-surface water-borne vehicles, and combinations thereof.

The presently disclosed aspects may, of course, be carried out in other ways than those specifically set forth herein without departing from essential characteristics of the presently disclosed aspects. The present aspects are to be considered in all respects as illustrative and not restrictive, and all changes coming within the meaning and equivalency range of the appended claims are intended to be embraced therein.

What is claimed is:

1. An X-ray backscatter detection apparatus comprising:
   a housing, said housing comprising a housing exterior, said housing configured to encase components, said components comprising:
      at least a plurality of electronic circuits; an X-ray source; and an integrated high voltage power supply;
   a photomultiplier tube, said photomultiplier tube configured to generate an electro-magnetic field, and said photomultiplier tube oriented externally of the housing and said at least one photomultiplier tube oriented proximate to the housing exterior;
   a scintillator detector oriented proximate to the housing exterior; and
   at least one deflection yoke, said at least one deflection yoke oriented proximate to said photomultiplier tube, and said at least one deflection yoke oriented proximate to the housing exterior.

2. The X-ray backscatter detection apparatus of claim 1, wherein said deflection yoke is configured to generate a predetermined countering electro-magnetic field, said predetermined countering electro-magnetic field configured to at least partially counter the electro-magnetic field generated by the photomultiplier tube.

3. The X-ray backscatter detection apparatus of claim 1, wherein the photomultiplier tube integrates the deflection yoke.

4. The X-ray backscatter detection apparatus of claim 1, wherein the photomultiplier tube comprises a plurality of deflection yokes, said plurality of deflection yokes coupled to the photomultiplier tube.

5. The X-ray backscatter detection apparatus of claim 1, wherein the deflection yoke obviates a plurality of components, said plurality of components comprising more than one of: a cooling device; a high voltage cable; a commutation cable, a control unit; a cable management device; or combinations thereof.

6. The X-ray backscatter detection apparatus of claim 1, wherein the X-ray backscatter detection apparatus comprises a physical footprint, said physical footprint further comprising a portable footprint, and wherein the X-ray backscatter detection apparatus is portable.

7. The X-ray backscatter detection apparatus of claim 1, wherein the deflection yoke comprises a predetermined amount of wire wound around the deflection yoke.

8. The X-ray backscatter detection apparatus of claim 1, wherein the deflection yoke is configured to generate a predetermined countering electro-magnetic field, said countering electro-magnetic field having a predetermined value.

9. The X-ray backscatter detection apparatus of claim 1, wherein said X-ray source and said integrated high voltage power supply are integrated within the housing.

10. A method of making an X-ray backscatter detection apparatus, the method comprising:
   integrating a plurality of X-ray backscatter detection components into a housing, said housing comprising a housing exterior, said plurality of X-ray backscatter detection components comprising: a high voltage power supply; a plurality of electronic circuits; and an X-ray generating source;
   orienting a scintillator detector proximate to the housing exterior;
   orienting a photomultiplier tube proximate to the scintillator detector; and
   orienting at least one deflector yoke proximate to the photomultiplier tube.

11. The method of claim 10, further comprising:
   coupling at least one deflection yoke to a photomultiplier tube; and
   wherein said deflection yoke is configured to generate a predetermined countering electro-magnetic field, said predetermined countering electro-magnetic field configured to at least partially counter an electro-magnetic field generated by the photomultiplier tube;
   generating a predetermined countering electro-magnetic field; and
   at least partially countering the electro-magnetic field generated by the photomultiplier tube.

12. The method of claim 10, further comprising:
   coupling a plurality of deflection yokes to the photomultiplier tube.

13. The method of claim 10, further comprising:
   coupling a plurality of deflection yokes to a plurality of photomultiplier tubes.

14. A method of non-destructively inspecting a substrate, said method comprising:
   orienting an X-ray backscatter detection apparatus proximate to a substrate, said X-ray backscatter detection apparatus comprising a housing, said housing comprising a housing exterior, said X-ray backscatter detection apparatus further comprising within the housing:
      an X-ray source;
      a high voltage power supply;
   orienting externally of the housing exterior:
      a photomultiplier tube, said photomultiplier tube configured to generate an electro-magnetic field;
      a deflection yoke oriented proximate to the photomultiplier tube, said deflection yoke configured to generate a predetermined countering electro-magnetic field;
      a scintillator detector;
   generating a predetermined electro-magnetic field;
   generating a predetermined at least partially countering electro-magnetic field;
   delivering an X-ray beam to the substrate;
   collecting an amount of X-ray backscatter at the scintillator detector;
   generating an image signal; and
   sending the image signal to a readout.

15. The method of claim 14, wherein said X-ray source and said high voltage power supply are oriented within the housing.

16. The method of claim 14, wherein said scintillator detector, said photomultiplier tube and said deflection yoke are oriented proximate to the housing exterior and are further oriented outside of the housing.

17. The method of claim 14, further comprising:
   coupling at least one deflection yoke to the photomultiplier tube.

18. The method of claim 14, further comprising:
   coupling a plurality of deflection yokes to the photomultiplier tube.

19. The method of claim 14, further comprising:
   coupling a plurality of deflection yokes to a plurality of photomultiplier tubes.

20. The method of claim 14, wherein the X-ray backscatter detection apparatus is a portable X-ray backscatter detection apparatus.

* * * * *